(12) United States Patent
Koenigsmann et al.

(10) Patent No.: US 8,546,591 B2
(45) Date of Patent: Oct. 1, 2013

(54) METHOD FOR PRODUCING CIS-ROSE OXIDE

(75) Inventors: Lucia Koenigsmann, Stuttgart (DE);
Juergen Schubert, Dirmstein (DE);
Andreas Walch, Schwaigern (DE);
Guenther Gottwald, Mannheim (DE);
Martin Kamasz, Mannheim (DE);
Ekkehard Schwab, Neustadt (DE);
Klaus-Peter Pfaff, Friedelsheim (DE);
Michael Slany, Kirchheim (DE)

(73) Assignee: BASF SE, Ludwigshafen (DE)

( * ) Notice: Subject to any disclaimer, the term of this patent is extended or adjusted under 35 U.S.C. 154(b) by 546 days.

(21) Appl. No.: 12/809,356

(22) PCT Filed: Dec. 17, 2008

(86) PCT No.: PCT/EP2008/067688
§ 371 (c)(1),
(2), (4) Date: Jun. 18, 2010

(87) PCT Pub. No.: WO2009/077550
PCT Pub. Date: Jun. 25, 2009

(65) Prior Publication Data
US 2010/0311988 A1 Dec. 9, 2010

(30) Foreign Application Priority Data
Dec. 19, 2007 (EP) ..................... 07123639

(51) Int. Cl.
*C07D 309/00* (2006.01)
*B01J 21/18* (2006.01)
*C07C 253/00* (2006.01)

(52) U.S. Cl.
USPC ........................ 549/356; 502/185; 558/323

(58) Field of Classification Search
USPC .......................... 549/356; 502/185; 558/323
See application file for complete search history.

(56) References Cited

U.S. PATENT DOCUMENTS

| 4,429,144 A | 1/1984 | Hoffman |
| 4,465,787 A | 8/1984 | Horner et al. |
| 4,536,347 A | 8/1985 | Horner et al. |
| 7,101,824 B2 | 9/2006 | Gerlach et al. |

FOREIGN PATENT DOCUMENTS

| EP | 0071787 A2 | 2/1983 |
| EP | 0082401 A1 | 6/1983 |
| EP | 1317959 A1 | 6/2003 |
| GB | 2036004 A | 6/1980 |
| WO | WO-79/00509 A1 | 8/1979 |
| WO | WO-97/00509 A1 | 1/1997 |

OTHER PUBLICATIONS

Tyman, et al., "The Reaction of 3-Alkene-1-ols with Aldehydes: A Synthesis of (±)-cis-2-(2'methyl-1'-propenyl)-4-methyltetrahydropyran," *Tetrahedron Letters*, No. 51, pp. 4507-4508 (1970).

*Primary Examiner* — Andrew D Kosar
*Assistant Examiner* — Raymond Covington
(74) *Attorney, Agent, or Firm* — Novak Druce Connolly Bove + Quigg LLP

(57) ABSTRACT

The present invention relates to a process for the preparation of cis-2-(2-methylprop-1-enyl)-4-methyltetrahydropyran comprising the catalytic hydrogenation of 2-(2-methylprop-1-enyl)-4-methylenetetrahydropyran in the presence of hydrogen and a heterogeneous catalyst comprising ruthenium on a support and subsequently bringing the compounds obtained in this way into contact with a strongly acidic cation exchanger.

19 Claims, No Drawings

METHOD FOR PRODUCING CIS-ROSE OXIDE

RELATED APPLICATIONS

This application is a national stage application (under 35 U.S.C. §371) of PCT/EP2008/067688, filed Dec. 17, 2008, which claims benefit of European Application No. 07123639.2, filed Dec. 19, 2007.

DESCRIPTION

The present invention relates to a process for the preparation of cis-2-(2-methylprop-1-enyl)-4-methyltetrahydropyran comprising the catalytic hydrogenation of 2-(2-methylprop-1-enyl)-4-methylenetetrahydropyran in the presence of hydrogen and a heterogeneous catalyst comprising ruthenium on a support and subsequently bringing the compounds obtained in this way into contact with a strongly acidic cation exchanger.

Cis-2-(2-methylprop-1-enyl)-4-methyltetrahydropyran is a valuable aroma chemical also referred to as rose oxide. It is usually produced in the form of a diastereomer mixture with the corresponding trans-configured compound, the specified cis-configured compound having proven to be the more valuable compound on account of having a better odor. Since said diastereomers can only be separated from one another with difficulty, especially when produced on an industrial scale, there is a continuing need for preparation processes in which the preferred cis-isomer (rose oxide) is formed as selectively as possible in a high yield.

In Tetrahedron Letters No. 51, 4507-4508, 1970, J. H. P. Tyman and B. J. Willis describe the acid-catalyzed reaction of 3-alken-1-ols with aldehydes, specifically the reaction of 3-methyl-2-buten-1-al with 2-methyl-1-buten-4-ol and subsequent dehydration. The intermediate obtained in this way and having an exocyclic methylene group was hydrogenated under homogeneous catalysis in the presence of $SnCl_2$/$H_2PTCl_6$ to give the racemic cis-2-(2'-methyl-1'-propenyl)-4-methyltetrahydropyran.

WO 79/00509 discloses a process for the preparation of mixtures, enriched with regard to the cis isomer, of cis- and trans-(2-methylprop-1-enyl)-4-methyltetrahydropyran by catalytic hydrogenation of the corresponding precursor having an exo-methylene group in the 4 position. Raney-nickel and palladium catalysts, specifically palladium on carbon, are specified as suitable hydrogenation catalysts. The isomer enrichment is achieved by treating the hydrogenation product with an acidic or Lewis-acidic reagent. Boron trifluoride is specified as preferred Lewis acid.

The hydrogenation described by way of example with Raney nickel with subsequent distillation produces a mixture of the cis and transisomers in a ratio of 4:6 in a yield of 87.9% of theory. This mixture is converted in the subsequent isomerization to an isomer mixture in the ratio of about 85:15 in a yield of 86.5% of theory.

EP 0 082 401 A1 discloses a process for the preparation of rose oxide comprising predominantly, i.e. to at least 85%, the Z isomer. The process involves hydrogenating 2-[2-methyl-prop-1-enyl]-4-methylenetetrahydropyran ("dehydrorose oxide") over a platinum dioxide or a platinum/carbon catalyst in the presence of a strongly acidic cation exchanger.

In the isomerizing hydrogenation described by way of example of dehydrorose oxide to rose oxide, a yield of up to 87% of theory with an isomer content of the E isomer of 90.5% and of the Z isomer of 7% is achieved.

Starting from this prior art, it was the object of the present invention to provide a process for the preparation of diastereomer-enriched rose oxide which can be carried out on an industrial scale in a manner which is easy to handle in terms of processing and with high overall yield coupled with the highest possible selectivity with regard to the desired cis-2-(2-methylprop-1-enyl)-4-methyltetrahydropyran. In the process it should be possible to use starting compounds and reagents and catalysts which are inexpensive, can be readily recovered and can easily be reused.

According to the invention, the object was achieved through the provision of a process for the preparation of cis-2-(2-methylprop-1-enyl)-4-methyltetrahydropyran of the formula (I)

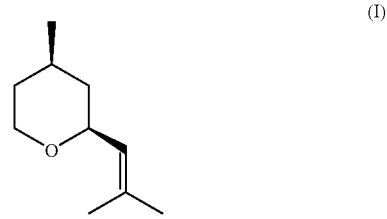

comprising the steps
a) catalytic hydrogenation of 2-(2-methylprop-1-enyl)-4-methylenetetrahydropyran of the formula (II)

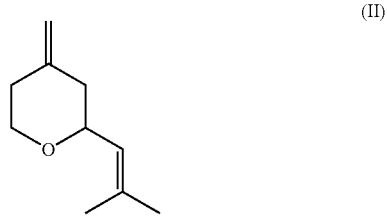

in the presence of hydrogen and a heterogeneous catalyst comprising ruthenium on a support to give a reaction mixture comprising the compound of the formula (I) and trans-2-(2-methylprop-1-enyl)-4-methyltetrahydropyran of the formula (III)

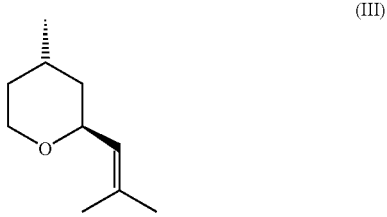

and
b) if appropriate separating off the compounds of the formulae (I) and (III) from the reaction mixture obtained according to step a) and
c) bringing the compounds of the formulae (I) and (III) obtained in step a) or b) into contact with a strongly acidic cation exchanger with isomerization of the compound of the formula (III) to give the compound of the formula (I).

The process according to the invention is suitable for the preparation of cis-2-(2-methylprop-1-enyl)-4-methyl-tetrahydropyran of the formula (I)

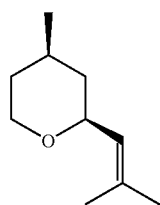

(I)

which is also referred to below as rose oxide and which is usually produced in the form of mixtures with its diastereomer trans-2-(2-methylprop-1-enyl)-4-methyltetrahydropyran of the formula (III)

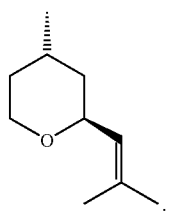

(III)

Within the context of a preferred embodiment, the process according to the invention relates to a process for the preparation of an isomer mixture of cis-2-(2-methylprop-1-enyl)-4-methyltetrahydropyran of the formula (I) and trans-2-(2'-methylprop-1-enyl)-4-methyltetrahydropyran of the formula (III). Within the context of a particularly preferred embodiment, the process according to the invention relates to a process for the preparation of an isomer mixture of cis-2-(2-methylprop-1-enyl)-4-methyl-tetrahydropyran of the formula (I) and trans-2-(2-methylprop-1-enyl)-4-methyl-tetrahydropyran of the formula (III) comprising, based on the amount of the isomer mixture, at least 70%, preferably at least 90% and particularly preferably 90 to 98%, of cis-2-(2-methylprop-1'-enyl)-4-methyltetrahydropyran of the formula (I) and at most 30%, preferably at most 10% and particularly preferably 2 to 10%, of trans-2-(2-methylprop-1-enyl)-4-methyltetrahydropyran of the formula (III).

The specified diastereomer mixture is produced here in the course of the preparation process according to the invention usually in a high chemical purity of generally 90% by weight or above, preferably 95 to 99.9% by weight and particularly preferably 97 to 99.5% by weight (in each case based on the sum of the two diastereomers).

According to the invention, the compounds of the formulae (I) and (III) are produced in racemic form. The formula images (I) and (III) accordingly serve to illustrate the relative configuration of the two stereo centers and in each case stand for the racemic mixtures of the respective enantiomer pairs. A starting material which can be used according to the invention is therefore also racemic 2-(2-methylprop-1-enyl)-4-methylenetetrahydropyran of the formula (II), which in principle can be prepared by any method and whose nature or purity is not subject to any specific requirements within the framework of that which is usual for synthetic purposes.

Within the scope of a preferred embodiment, the process according to the invention also comprises, as an additional upstream process step, the provision of 2-(2-methylprop-1-enyl)-4-methylenetetrahydropyran (dehydrorose oxide) of the formula (II) by reacting 3-methylbut-3-en-1-ol (isoprenol) of the formula (IV)

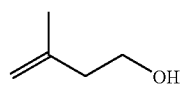

(IV)

with 3-methylbut-2-en-1-al (prenal) of the formula (V)

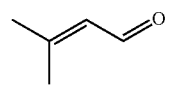

(V)

with the release of water in the presence of an acid and in the presence of a solvent which forms an azeotrope with water.

Within the context of a particularly preferred embodiment of the process according to the invention, the procedure involves separating off the water released during the aforementioned reaction of 3-methylbut-3-en-1-ol (isoprenol) of the formula (IV) with 3-methyl-but-2-en-1-al (prenal) of the formula (V) from the reaction mixture by azeotropic distillation with the solvent used. For this, it is possible to use either individual solvents which form an azeotrope with water or mixtures of different solvents. For this, preference is given to using those solvents which form an azeotrope with water which has a lower boiling point than the particular solvent or solvent mixture itself, preferably those whose azeotropic boiling point is in the range from about 60° C. to about 120° C., particularly preferably in the range from about 65° C. to about 90° C. Solvents which can preferably be used within the context of this embodiment, may be, for example, those selected from the group of the solvents comprising ethanol, benzene, tetrachloromethane, ethyl acetate, toluene, chloroform, n-heptane, cyclohexane and methylcyclohexane. Particularly preferred solvents which form an azeotrope with water may be those selected from the group comprising toluene, chloroform, n-heptane, cyclohexane and methylcyclohexane. Very particularly preferred solvents are toluene and n-heptane, especially preferably toluene.

The separating off of the water released during the reaction by azeotropic distillation can be carried out by methods known per se to the person skilled in the art and/or using the devices suitable for this purpose, such as, for example, using a water separator.

The amount of solvent or solvent mixture chosen in each case to be used within the context of the aforementioned azeotropic distillation can be chosen within a wide range and is usually governed by the chosen reaction conditions and also the device used for separating off the water. It has proven to be advantageous to use the selected solvent or solvent mixture in a quantitative ratio, based on the total amount of the starting materials 3-methylbut-3-en-1-ol (isoprenol) and 3-methylbut-2-en-1-al (prenal) used, of from about 1:1 to about 2:1, preferably about 1:1 to about 1.5:1, i.e. in a slight excess. After carrying out the reaction, the solvent can generally be separated off easily and can be reused in the course of further reactions.

The provision of dehydrorose oxide of the formula (II) to be optionally carried out by reacting 3-methylbut-3-en-1-ol (isoprenol) and 3-methylbut-2-en-1-al (prenal) is also carried out in the presence of an acid. Suitable acids for this have proven to be both organic and inorganic acids, such as, for example p-toluenesulfonic acid, trifluoroacetic acid or else alkali metal hydrogensulfate. Within the context of a preferred embodiment, the reaction of 3-methylbut-3-en-1-ol with 3-methylbut-2-en-1-al is carried out in the presence of an alkali metal hydrogensulfate, such as, for example sodium hydrogensulfate or potassium hydrogensulfate, preferably sodium hydrogensulfate.

The selected acid is preferably used in catalytic amounts, usually, based on the total amount of the starting materials 3-methylbut-3-en-1-ol and 3-methylbut-2-en-1-al to be reacted, in an amount of from about 0.01 to about 1% by weight.

The reaction for the preparation of dehydrorose oxide by condensing isoprenol with prenal is carried out usually, and depending on the selected solvent or solvent mixture and the selected acid, at temperatures in the range from about 60° C. to 150° C., preferably in the range from about 70° C. to 120° C. and is then as a rule largely concluded rapidly, often after about 24 hours or even earlier. The reaction mixture obtained can be worked up by methods known to the person skilled in the art, for example by extractive methods, if appropriate following neutralization of the acid used. The dehydrorose oxide of the formula (II) thus obtained as crude product can then be further purified, for example by chromatography or preferably by (fractional) distillation, during which in particular the nerol oxide usually produced as by-product and also further high-boiling secondary components can be separated off.

The catalytic hydrogenation of 2-(2-methylprop-1-enyl)-4-methylenetetrahydropyran of the formula (II) to be carried out according to process step a) of the process according to the invention to give a reaction mixture comprising the compound of the formula (I) and the compound of the formula (III) is carried out in the presence of hydrogen and in the presence of a heterogeneous catalyst comprising ruthenium on a support. Preference is given here to using those catalysts which comprise ruthenium on a carbon support. Said catalysts can, if appropriate, also comprise further metals, for example in the form of dopings. In this connection, the support materials familiar to the person skilled in the art, such as, for example, $SiO_2$, $Al_2O_3$, graphites, carbon blacks or activated carbon are specified under the term support. Among these, preferred supports are to be understood as meaning carbon supports, i.e. carbon-based support materials familiar to the person skilled in the art, such as, for example, activated carbon, graphites or carbon blacks. A preferred carbon support which may be mentioned is activated carbon such as, for example, NORIT® SX Plus.

Within the context of a preferred embodiment, process step a) is carried out in the presence of a catalyst comprising ruthenium doped with iron on a support. Particularly preferably, process step a) according to the invention is carried out in the presence of a catalyst comprising ruthenium doped with iron on a carbon support. Such catalysts are known and described, for example, in EP 0 071 787 and EP 1 317 959, to which reference is made here in this regard in their entirety. Catalysts which are to be used particularly preferably according to the invention are those which, in each case based on the finished catalyst, comprise 0.1 to 10% by weight of ruthenium and 0.1 to 5% by weight of iron, particularly preferably 4 to 6% by weight of ruthenium and 0.5 to 1.5% by weight of iron, on a carbon support, preferably on activated carbon.

The catalytic hydrogenation to be carried out according to the invention in accordance with process step a) is usually carried out at temperatures in the range from about 50° C. to about 150° C., preferably in the range from about 70° C. to about 130° C. and at absolute pressures in the range from about 1 to about 25 bar, preferably in the range from about 2 bar to about 10 bar. The catalytic hydrogenation to be carried out according to the invention can also be carried out in the presence of solvents which are inert under the reaction conditions, such as, for example, methanol, hexane, tetrahydrofuran.

The hydrogen to be used can be used in pure form or if desired also in the form of mixtures with other, preferably inert, gases such as nitrogen or argon. Preference is given to using hydrogen in undiluted form.

After separating off the catalyst used, for example by filtration and, if appropriate, separating off the solvent used, preferably by distillation, a reaction mixture is obtained which comprises the diastereomeric compounds of the formulae (I) and (III) and if appropriate can also comprise further impurities, undesired secondary components or else residues of unreacted starting material.

According to process step b), to be carried out optionally, of the process according to the invention, if desired, a separating off of the compounds of the formulae (I) and (III) from the reaction mixture obtained according to step a) can be carried out. For this purpose, the methods of material separation which appear suitable to the person skilled in the art are available, such as, for example chromatography or preferably distillation. Suitable distillation apparatuses which may be mentioned are, for example, devices for short-path distillation, such as, for example, thin-film evaporators or else filled or packed columns, and also plate columns.

The mixture of the compounds of the formula (I) and (III), obtained in this way according to process step a) or following purification according to the optional process step b), is then brought into contact, according to the separate process step c), with a strongly acidic cation exchanger with isomerization of the compound of the formula (III) to give the compound of the formula (I).

In this connection, the compound of the formula (III), i.e. the trans-diastereomer, can be converted completely or partially, usually partially, into its diastereomer of the formula (I), i.e. into the cis-diastereomer. Consequently, after carrying out the separate process step c) of the process according to the invention, mixtures of the compounds of the formulae (I) and (III) are obtained which have a higher content of the desired compound of the formula (I) than the mixtures initially obtained by process step a) and/or b). In this way, preferably the aforementioned diastereomer-enriched mixtures of cis-2-(2-methylprop-1-enyl)-4-methyltetrahydropyran of the formula (I) and trans-2-(2-methylprop-1-enyl)-4-methyltetrahydropyran of the formula (III) are obtained, comprising, based on the amount of the isomer mixture, at least 70%, preferably at least 90% and particularly preferably 90 to 98% of cis-2-(2-methylprop-1-enyl)-4-methyltetrahydropyran of the formula (I) and at most 30%, preferably at most 10% and particularly preferably 2 to 10% of trans-2-(2-methylprop-1-enyl)-4-methyltetrahydropyran of the formula (III).

The isomerization according to process step c) of the process according to the invention takes place in the presence of a strongly acidic ion exchanger, i.e. a strongly acidic cation exchanger such as, for example, LEWATIT® S100, LEWATIT® SP112, LEWATIT® S115, LEWATIT® SP1080, LEWATIT® SC102, LEWATIT® SPC118, LEWATIT® CNP 80, LEWATIT® HD 5, AMBERLITE® IR 120, AMBERLITE® IR200, AMBERLYST™ 15, Bay. KAT. K 2431, Bay. KAT. K 2621, DOWEX® 50, PERMUTIT® RS, WOFATIT® KPS 200, DUOLITE™ C-3, DUOLITE™ C-10, DUOLITE™ C-25, WOFATIT® F, WOFATIT® D, WOFATIT® P, Zeoxex (Zeo karb H), Nalcite HCR, Nalcite HGR, Nalcite HDR, PERMUTIT® Q and PERMUTIT® RS, SERDROLIT® Red. The selected strongly acidic cation exchangers can also be used in the form of mixtures of two or more different cation exchangers. According to the Invention, preference is given to using the cation exchangers LEWATIT® SP112 and/or AMBERLYST™ 15.

Within the context of a preferred embodiment of the process according to the invention, the selected cation exchanger is used in the form of a fixed bed, via which the diastereomer mixture to be reacted, obtained from process step a) or b), is passed as such or in the form of a solution in a suitable solvent which is inert under the reaction conditions. Preferably, the mixture to be isomerized is brought into contact in undiluted form with the selected strongly acidic cation exchanger. In this connection, the fixed bed can be arranged, for example, in the form of a bed of the selected cation exchanger in a reactor tube, with the mixture to be isomerized being passed through the reactor tube filled in this way. To this end, the reactors can be operated in all modes of operation which appear suitable to a person skilled in the art, such as, for example, in liquid-phase mode or, according to the invention, preferably in trickle mode, where the mixture to be isomerized is trickled onto a bed of the selected cation exchanger.

In this way, the continuous reaction procedure preferred according to the invention within the context of process step c) is also possible. With the context of a preferred embodiment, process step c) is therefore carried out continuously. Here, the mixture comprising the compounds of the formula (I) and (III) that is to be isomerized is passed continuously to the cation exchanger, for example through introduction into a reactor filled with cation exchanger, and is continuously separated off again from the same, for example by discharging the isomerized mixture from the reactor.

The mixture of the compounds of the formulae (I) and (III) to be isomerized can also be repeatedly brought into contact one after the other with the selected strongly acidic cation exchanger or else with different strongly acidic cation exchangers, for example by returning the diastereomer-enriched isomer mixture discharged from the fixed-bed reactor as described above to the same reactor. It is also possible to pass through several such reactors, which may, if desired, also be filled with different cation exchangers, one after the other in order, in so doing, to arrive at the desired diastereomer ratio as described above.

The isomerization according to process step c) is usually carried out at temperatures of from about 0° C. to about 100° C., preferably at about 20 to about 80° C.

The examples below serve to illustrate the invention without limiting it in any way:

EXAMPLE 1

In a reaction vessel with a volume of 5 l and provided with stirrer, water separator, condenser and a metering pump, 2000 g of toluene and 1.5 g of $NaHSO_4$ (as 10% strength aqueous solution) were initially introduced and 7.67 mol (660 g) of 3-methylbut-3-en-1-ol and 7.67 mol (643.5 g) of 3-methylbut-2-en-1-al were metered in over the course of 16 h at 110 to 115° C. The water was continuously removed azeotropically from the reaction mixture with toluene and the toluene was returned. The reaction mixture was then stirred for a further 5.5 h at 115° C. The resulting reaction mixture was then washed with 278 g of 2% strength NaOH solution. The toluene was distilled off at a pressure of 200 mbar over a 30 cm-long column, filled with Raschig rings. The conversion to the dehydrorose oxide (DHR) was 62.7% of theory. Finally the DHR was separated from nerol oxide and high-boiling secondary components by distillation and obtained with a purity of >99%.

EXAMPLE 2

The dehydrorose oxide (DHR) obtained in this way was carried out in a 500 ml Büchi Laboratory autoclave at a hydrogen pressure of 4 bar (experiment a)) or 3 bar (experiments b) and d)) and a temperature of 100° C., with vigorous stirring. Following completion of the reaction, the catalyst was filtered off.

EXAMPLE 2a 74.2 g of dehydrorose oxide dissolved in 112 g of methanol were hydrogenated as described above in the presence of 1.1 g of a catalyst of 5% by weight of ruthenium and 1% by weight of iron on activated carbon. The reaction mixture obtained was analyzed by gas chromatography at the times indicated in table 1 (GC method: column: DB-210, 30 m, 0.32 mm, 0.5 µm; 50° C., at 3° C./min to 230° C.). The results given in table 1 were obtained (in each case in GC area %, conversion and selectivity in each case in %):

TABLE 1

| Time (min) | 30 | 60 | 180 | 240 | 300 | 360 |
|---|---|---|---|---|---|---|
| Dehydrorose oxide | 75.57 | 73.63 | 48.53 | 12.85 | 6.74 | 0.00 |
| cis-Rose oxide | 7.32 | 8.06 | 16.74 | 28.94 | 31.08 | 32.32 |
| trans-Rose oxide | 13.98 | 15.28 | 30.68 | 52.44 | 55.99 | 57.79 |
| Conversion | 24.23 | 26.37 | 51.47 | 87.15 | 93.26 | 100 |
| Selectivity | 87.91 | 88.51 | 92.13 | 93.38 | 93.36 | 90.11 |

EXAMPLE 2b 270 g of dehydrorose oxide were hydrogenated without the addition of a solvent in the presence of 1% by weight of the catalyst described under example 2a). This gave the results shown in table 2:

TABLE 2

| Time (min) | 30 | 60 | 90 | 110 |
|---|---|---|---|---|
| Dehydrorose oxide | 59.28 | 20.03 | 5.10 | 0.33 |
| cis-Rose oxide | 10.48 | 20.64 | 23.92 | 24.55 |
| trans-Rose oxide | 25.07 | 50.38 | 58.19 | 59.08 |
| Conversion | 40.72 | 79.97 | 94.90 | 99.67 |
| Selectivity | 87.30 | 88.80 | 86.53 | 83.90 |

EXAMPLE 2c

The catalyst used in the above-described example 2b) and separated off by filtration was reused in this experiment under otherwise unchanged conditions. The results shown in table 3 were obtained:

TABLE 3

| Time (min) | 30 | 60 | 90 | 110 |
|---|---|---|---|---|
| Dehydrorose oxide | 61.65 | 21.45 | 1.77 | 0.11 |
| cis-Rose oxide | 9.82 | 20.46 | 25.06 | 24.88 |
| trans-Rose oxide | 23.88 | 50.35 | 61.50 | 60.51 |
| Conversion | 38.35 | 78.55 | 98.23 | 99.89 |
| Selectivity | 87.87 | 90.15 | 88.12 | 85.48 |

EXAMPLE 3

Isomerization of Cis/Trans Rose Oxide

In a 1 l flask, 452.4 g of a mixture of cis- and trans-rose oxide (ratio 0.4:1) were stirred with 4.5 g of ion exchanger SP112 H-form at 50° C. over a total experiment time of 6 h.

The ion exchanger LEWATIT® SP112 H-form was washed several times prior to use with methanol until free from water. The results ascertained by gas chromatography are shown in table 4:

TABLE 4

| Experiment time [h] | Conversion of trans-rose oxide [%] | Selectivity to cis-rose oxide [%] | cis/trans ratio [x:1] |
|---|---|---|---|
| 0 | 0.0 | 0.0 | 0.4 |
| 1 | 56.5 | 81.5 | 2.0 |
| 1.7 | 69.3 | 78.2 | 3.1 |
| 3.25 | 80.7 | 72.6 | 5.2 |
| 4 | 85.2 | 69.4 | 6.8 |
| 5 | 88.7 | 65.0 | 8.8 |
| 6 | 90.3 | 62.0 | 10.0 |

EXAMPLE 4

Isomerization of Cis/Trans Rose Oxide by Means of Fixed-Bed Ion Exchanger

The reactor used was a heated reactor tube made of stainless steel (length 200 mm; inner diameter 6 mm) filled with 3 g of ion exchanger LEWATIT® SP112 H-form and equipped with a feed pump for the rose oxide (30 g) and with a storage container with sampling. The reactor was operated in trickle-flow mode. The rose oxide was circulated at 55° C. over the fixed bed until a ratio of cis- to trans-rose oxide of >10:1 was reached. The gas chromatographically ascertained results listed in table 5 were obtained:

TABLE 5

| Experiment time [h] | Conversion of trans-rose oxide [%] | Selectivity to cis-rose oxide [%] | cis/trans ratio [x:1] |
|---|---|---|---|
| 0 | 0.0 | 0.0 | 2.3 |
| 1 | 44.6 | 73.8 | 4.7 |
| 3 | 67.0 | 79.7 | 8.5 |
| 5 | 75.4 | 78.1 | 11.6 |

After 5 hours, a ratio of cis- to trans-rose oxide of 11.6:1 was reached. Finally, the rose oxide obtained was separated from secondary components by distillation. This gave a yield after distillation of 92.12% of cis-rose oxide and 91.67% of trans-rose oxide.

The invention claimed is:

1. A process for the preparation of cis-2-(2-methylprop-1-enyl)-4-methyltetrahydropyran of the formula (I)

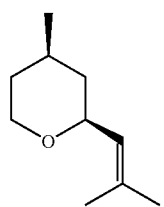

(I)

comprising the steps a) catalytic hydrogenation of 2-(2-methylprop-1-enyl)-4-methylenetetrahydropyran of the formula (II)

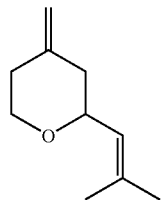

(II)

in the presence of hydrogen and a heterogeneous catalyst comprising ruthenium on a support to give a reaction mixture comprising the compound of the formula (I) and trans-2-(2-methylprop-1-enyl)-4-methyltetrahydropyran of the formula (III)

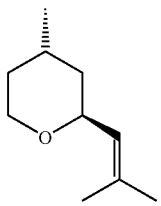

(III)

and b) if appropriate separating off the compounds of the formulae (I) and (III) from the reaction mixture obtained according to step a) and c) bringing the compounds of the formulae (I) and (III) obtained in step a) or b) into contact with a strongly acidic cation exchanger with isomerization of the compound of the formula (III) to give the compound of the formula (I).

2. The process of claim 1, additionally comprising the provision of the compound of the formula (II) by reacting 3-methylbut-3-en-1-ol with 3-methylbut-2-en-1-al with the release of water in the presence of an acid and a solvent which forms an azeotrope with water.

3. The process of claim 2, wherein the water released during the reaction of 3-methylbut-3-en-1-ol with 3-methylbut-2-en-1-al is separated from the reaction mixture by azeotropic distillation with the solvent used.

4. The process of claim 2, wherein a solvent which forms an azeotrope with water, selected from the group of solvents comprising toluene, chloroform, n-heptane, cyclohexane, and methylcyclohexane, is used.

5. The process of claim 2, wherein the reaction of 3-methylbut-3-en-1-ol with 3-methylbut-2-en-1-al is carried out in the presence of p-toluenesulfonic acid, trifluoroacetic acid or an alkali metal hydrogensulfate.

6. The process of claim 2, wherein an alkali metal hydrogensulfate is used as acid.

7. The process of claim 2, wherein sodium hydrogensulfate is used as acid.

8. The process of claim 1, wherein step a) is carried out in the presence of a catalyst comprising ruthenium on a carbon support.

9. The process of claim 1, wherein step a) is carried out in the presence of a catalyst comprising ruthenium doped with iron on a support.

10. The process of claim 1, wherein step a) is carried out in the presence of a catalyst which, in each case based on the finished catalyst, comprises 0.1 to 10% by weight of ruthenium and 0.1 to 5% by weight of iron on a carbon support.

11. The process of claim 1, wherein, in step c), the strongly acidic cation exchanger used is Lewatit® SP 112 and/or Amberlyst™ 15.

12. The process of claim 1, wherein the cation exchanger is used in the form of a fixed bed.

13. The process of claim 1, wherein process step c) is carried out continuously.

14. The process of claim 1, wherein process step c) is carried out such that the mixture of the compounds of the formulae (I) and (III) to be isomerized is brought into contact several times in succession with the strongly acidic cation exchanger or else with different strongly acidic cation exchangers.

15. A process for the preparation of cis-2-(2-methylprop-1-enyl)-4-methyltetrahydropyran of the formula (I)

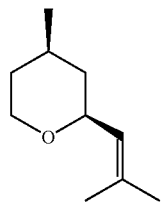

(I)

comprising catalytically hydrogenating 2-(2-methylprop-1-enyl)-4-methylenetetrahydropyran of the formula (II)

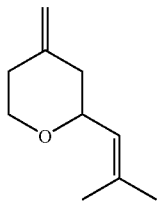

(II)

in the presence of hydrogen and a heterogeneous catalyst comprising ruthenium on a support to give a reaction mixture comprising the compound of the formula (I) and trans-2-(2-methylprop-1-enyl)-4-methyltetrahydropyran of the formula (III)

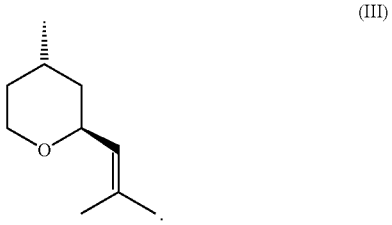

(III)

16. The process of claim 15, wherein the water released during the reaction of 3-methylbut-3-en-1-ol with 3-methylbut-2-en-1-al is separated from the reaction mixture by azeotropic distillation with the solvent used.

17. The process of claim 15, wherein the catalytic hydrogenation is carried out in the presence of a catalyst comprising ruthenium on a carbon support.

18. The process of claim 15, wherein the catalytic hydrogenation is carried out in the presence of a catalyst comprising ruthenium doped with iron on a support.

19. The process of claim 15, wherein the catalytic hydrogenation is carried out in the presence of a catalyst which, in each case based on the finished catalyst, comprises 0.1 to 10% by weight of ruthenium and 0.1 to 5% by weight of iron on a carbon support.

* * * * *